(12) United States Patent
Temple

(10) Patent No.: US 11,395,775 B1
(45) Date of Patent: Jul. 26, 2022

(54) PAD STORAGE AND DISPENSING DEVICE

(71) Applicant: Jonathan Temple, Middlesex, NJ (US)

(72) Inventor: Jonathan Temple, Middlesex, NJ (US)

(\*) Notice: Subject to any disclaimer, the term of this patent is extended or adjusted under 35 U.S.C. 154(b) by 0 days.

(21) Appl. No.: 17/318,044

(22) Filed: May 12, 2021

(51) Int. Cl.
*A61F 15/00* (2006.01)

(52) U.S. Cl.
CPC .................... *A61F 15/001* (2013.01)

(58) Field of Classification Search
CPC ....................................... A61F 15/001
See application file for complete search history.

(56) References Cited

U.S. PATENT DOCUMENTS

| | | | |
|---|---|---|---|
| 1,890,295 A | 12/1932 | Jacobs | |
| 4,053,242 A | 10/1977 | Mast, Jr. | |
| 5,054,619 A * | 10/1991 | Muckenfuhs | B65D 85/07 |
| | | | 206/83.5 |
| D347,344 S | 5/1994 | Schumaker | |
| 6,213,345 B1 * | 4/2001 | Plank | B65D 83/0894 |
| | | | 221/48 |
| 6,279,776 B1 | 8/2001 | Finkletaub | |
| 8,152,022 B2 | 4/2012 | Nygaaerd-Petersen | |
| 9,283,128 B2 | 3/2016 | Ulrich | |
| 10,207,858 B2 * | 2/2019 | Tan | B65D 75/5827 |
| 2002/0092789 A1 * | 7/2002 | Sauer | B65D 5/4208 |
| | | | 206/806 |
| 2009/0314794 A1 * | 12/2009 | Zylka | A47K 10/3827 |
| | | | 221/45 |
| 2010/0065576 A1 | 3/2010 | Verheij | |
| 2011/0297693 A1 * | 12/2011 | Crabill | B65D 5/3614 |
| | | | 221/45 |
| 2020/0069121 A1 | 3/2020 | Boelti | |

FOREIGN PATENT DOCUMENTS

WO     WO2012031600     3/2012

\* cited by examiner

*Primary Examiner* — Gene O Crawford
*Assistant Examiner* — Ayodeji T Ojofeitimi

(57) ABSTRACT

A pad storage and dispensing device for individually dispensing pads from a tube includes a tube, which has opposed ends that are closed. A plurality of pads is positioned in the tube. A pair of perforation lines and a pair of voids are positioned in the tube. The perforation lines are parallel and are perpendicular to the opposed ends. Each void extends from a respective opposing end of the pair of perforation lines. The voids and the perforation lines define a panel. A user can insert a digit of their hand into a void to separate the panel from the tube, which defines an opening. A sheet engaged to an inner surface of the tube extends across the opening. The user can insert digits of their hand into a slit, which is positioned in the sheet, to grasp and to pull a pad to remove the pad from the tube.

12 Claims, 6 Drawing Sheets

PAD STORAGE AND DISPENSING DEVICE

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to dispensing devices and more particularly pertains to a new dispensing device for individually dispensing pads from a tube. The present invention discloses a dispensing devices comprising a closed ended tube having a plurality of pads positioned therein. The pads are dispensed from the tube through an opening in a side of the tube, which is covered with a sheet. Digits of a hand of a user can be inserted through a slit in the sheet to grasp a pad and pull it through the slit.

(2) Description of Related Art Including Information Disclosed Under 37 CFR 1.97 and 1.98

The prior art relates to dispensing devices. Prior art dispensing devices may comprise tubes having hinged bottoms, open or partially open bottoms, or slots positioned proximate to their bottoms. What is lacking in the prior art is a dispensing devices comprising a closed ended tube having a plurality of pads positioned therein. The pads are dispensed from the tube through an opening in a side of the tube, which is covered with a sheet. Digits of a hand of a user can be inserted through a slit in the sheet to grasp a pad and pull it through the slit.

(h) BRIEF SUMMARY OF THE INVENTION

An embodiment of the disclosure meets the needs presented above by generally comprising a tube, which has opposed ends that are closed. A plurality of pads is positioned in the tube. A pair of perforation lines is positioned in the tube. The perforation lines are parallel and are perpendicular to the opposed ends. Each of a pair of voids is positioned in the tube and extends from a respective opposing end of the pair of perforation lines. The voids and the perforation lines define a panel. A respective void is configured for insertion of a digit of a hand of a user, positioning the user to separate the panel from the tube, which defines an opening. A sheet is engaged to an inner surface of the tube and extends across the opening. A slit is positioned in the sheet and is configured for insertion of digits of the hand of the user. The user is positioned to grasp and to pull a respective pad to remove the respective pad from the tube through the slit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
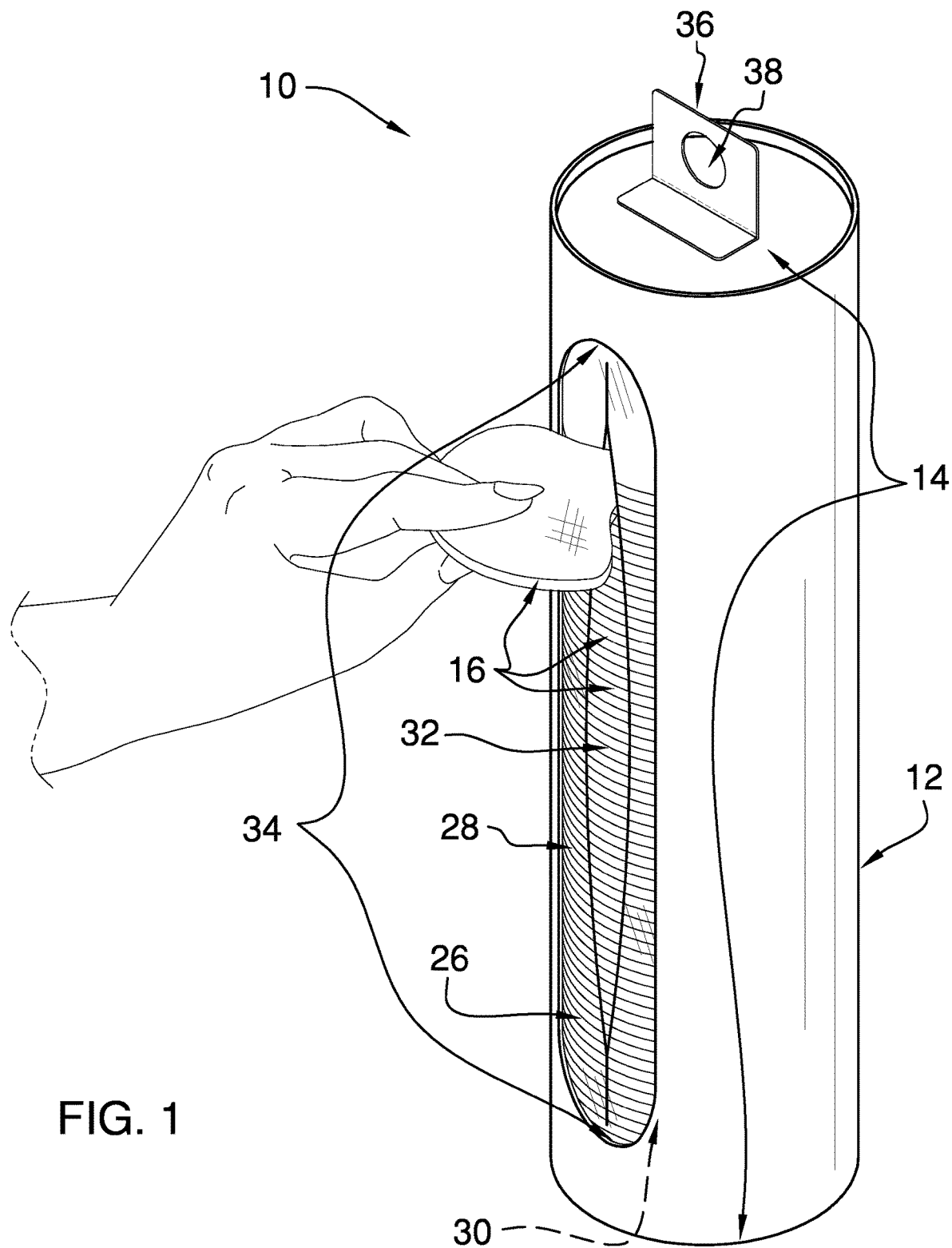
FIG. 1 is an in-use view of a pad storage and dispensing device according to an embodiment of the disclosure.

With reference now to the drawings, and in particular to FIGS. 1 through 6 thereof, a new dispensing device embodying the principles and concepts of an embodiment of the disclosure and generally designated by the reference numeral 10 will be described.

Figure 2:
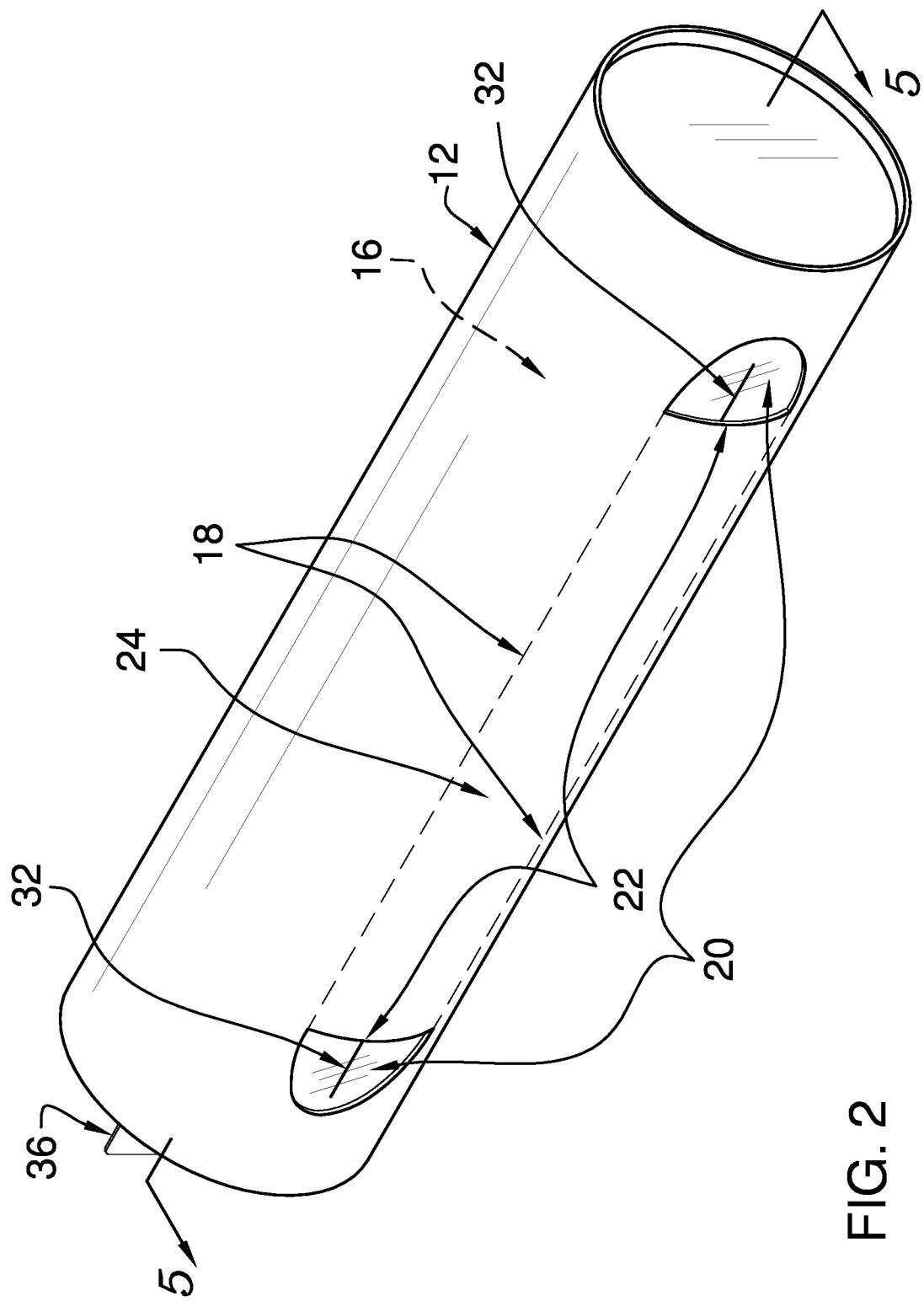
FIG. 2 is an isometric perspective view of an embodiment of the disclosure.
Figure 3:
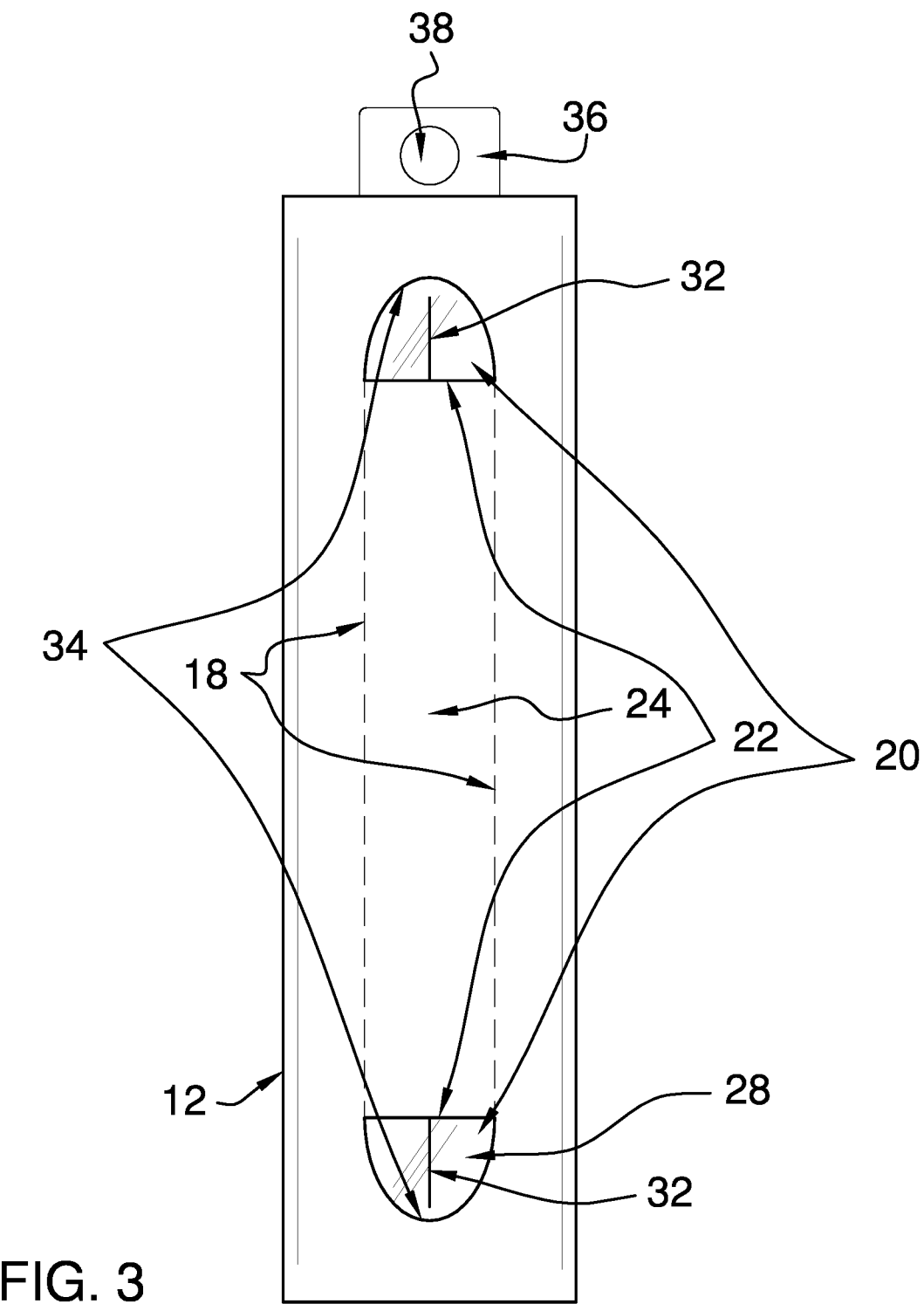
FIG. 3 is a front view of an embodiment of the disclosure.
Figure 4:
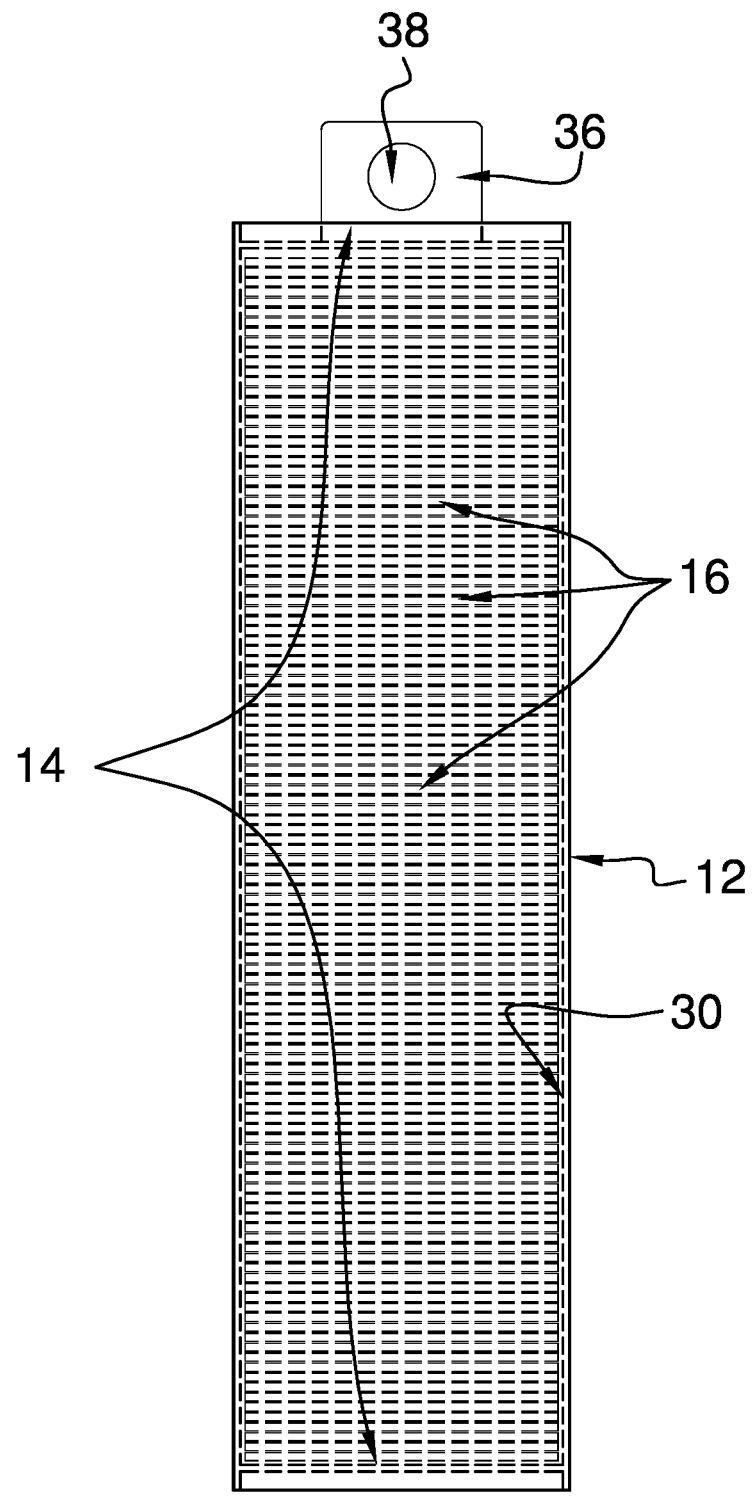
FIG. 4 is a back view of an embodiment of the disclosure.
Figure 5:
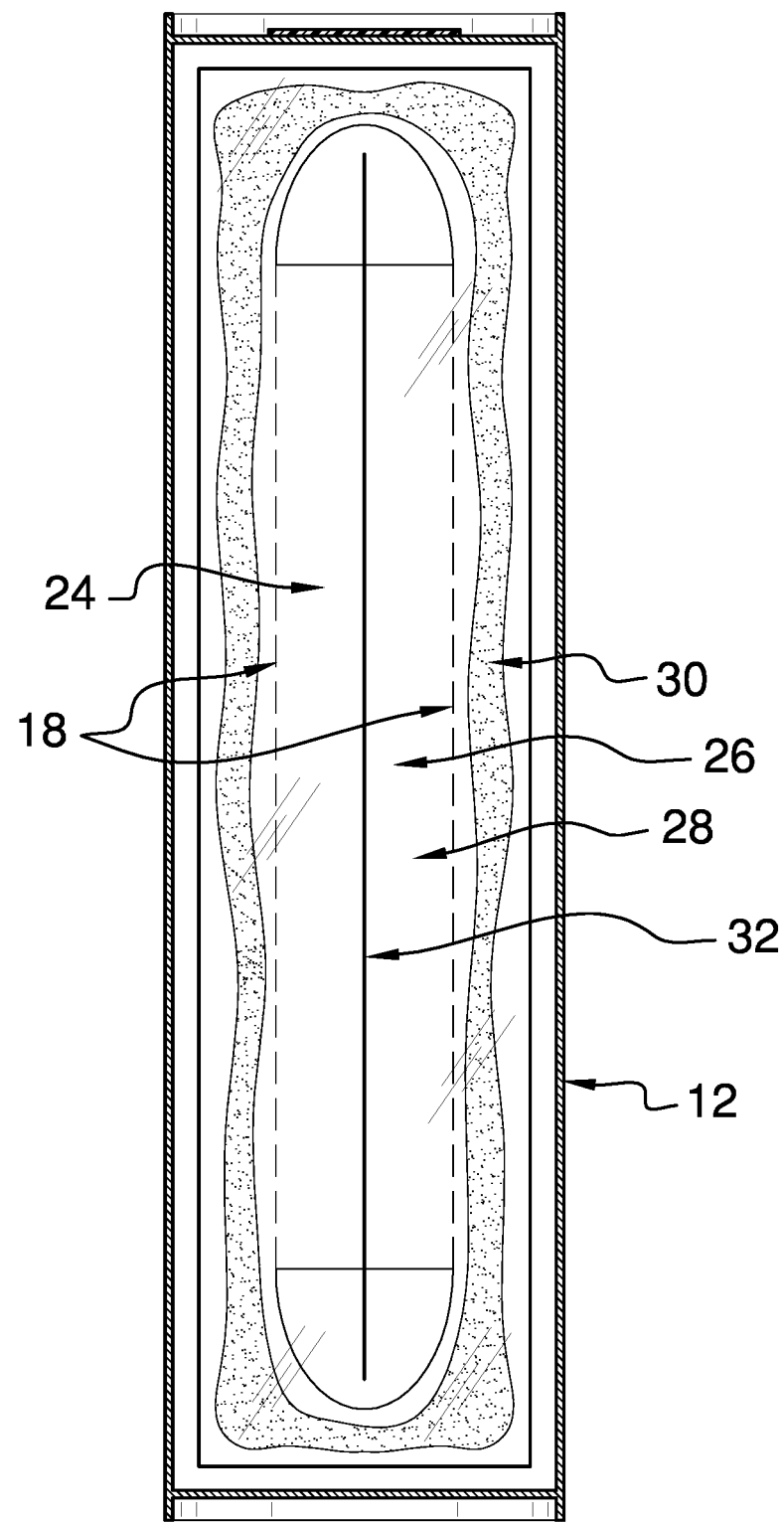
FIG. 5 is a cross-sectional view of an embodiment of the disclosure.
Figure 6:
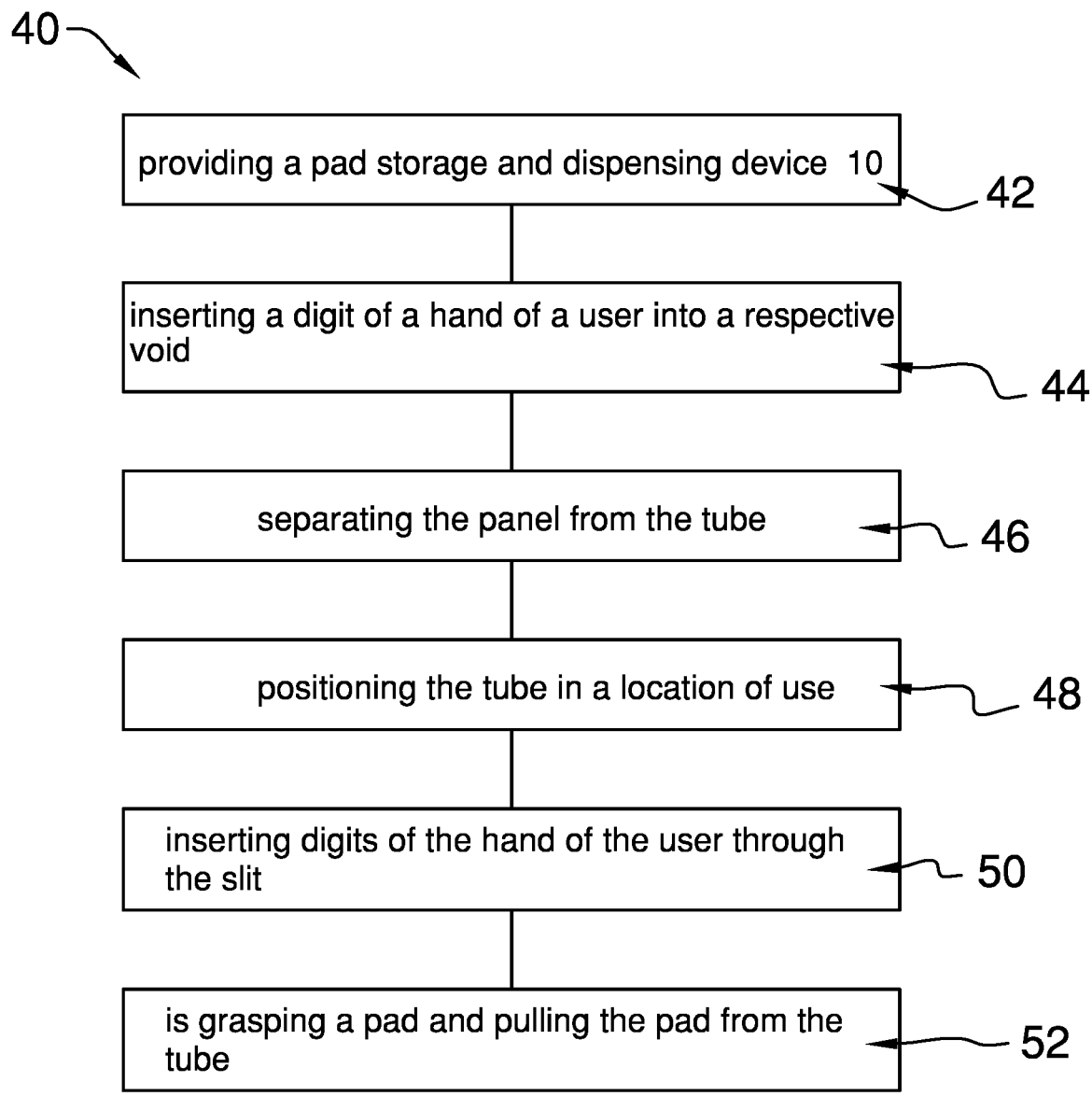
FIG. 6 is a schematic view of a method consistent with the disclosure.

As best illustrated in FIGS. 1 through 6, the pad storage and dispensing device 10 generally comprises a tube 12, which has opposed ends 14 that are closed. A plurality of pads 16 is positioned in the tube 12, as shown in FIGS. 1 and 4. The tube 12 may be cylindrical and the pads 16 may be circular, as shown in FIG. 1, although the present invention also anticipates the pads 16 being square, oval, and the like, with the tube 12 being complementarily shaped. The tube 12 comprises paperboard or other semirigid material, such as, but not limited to, card stock, plastic, and the like.

A pair of perforation lines 18 is positioned in the tube 12, as shown in FIGS. 2 and 3. The perforation lines 18 are parallel and are perpendicular to the opposed ends 14. Each of a pair of voids 20 is positioned in the tube 12 and extends from a respective opposing end 22 of the pair of perforation lines 18. The voids 20 and the perforation lines 18 define a panel 24. The voids 20 are arcuate distal from the opposing ends 22 of the pair of perforation lines 18 so that the voids are complementary to an end of a digit of a hand of a user. A respective void 20 is configured for insertion of the digit of the hand of the user, positioning the user to separate the panel 24 from the tube 12, which defines an opening 26.

A sheet 28 is engaged to an inner surface 30 of the tube 12 and extends across the opening 26. The sheet 28 comprises elastomer and thus is resiliently deformable. The sheet 28 may be substantially transparent, so as to allow visualization of the pads 16 in the tube 12. The sheet 28 may be adhesively engaged to the tube 12, although the present invention also anticipates the sheet 28 being integral to the tube 12.

A slit 32 is positioned in the sheet 28 and is configured for insertion of digits of the hand of the user. The slit 32 extends from proximate to opposed limits 34 of the opening 26. The user is positioned to grasp and to pull a respective pad 16 to remove the respective pad 16 from the tube 12 through the slit 32.

A tab 36 may be engaged to and extend from a respective opposed end 14 of the tube 12. A hole 38 is positioned in the tab 36 and is complementary to a rod of a display unit (not shown). The hole 38 is configured for selective insertion of the rod to removably engage the tube 12 to the display unit. The tab 36 may be perforated proximate to the tube 12 so that the tab 36 is configured to be selectively torn from the tube 12.

In use, the pad storage and dispensing device 10 enables a method 40 for storing and dispensing pads 16. The method 40 comprises a first step 42 of providing a pad storage and dispensing device 10 according to the specification above. A second step 44 of the method 40 is inserting a digit of a hand of a user into a respective void 20 and in between the panel 24 and the sheet 28. A third step 46 of the method 40 is separating the panel 24 from the tube 12. A fourth step 48 of the method 40 is positioning the tube 12 in a location of use. A fifth step 50 of the method 40 is inserting digits of the hand of the user through the slit 32 and into the tube 12. A sixth step 52 of the method 40 is grasping a respective pad 16 and pulling the respective pad 16 from the tube 12 through the slit 32.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pad storage and dispensing device comprising:
    a tube having opposed ends, the opposed ends being closed;
    a plurality of pads positioned in the tube;
    a pair of perforation lines positioned in the tube, the perforation lines of the pair of perforation lines being parallel and perpendicular to the opposed ends,
    a pair of voids positioned in the tube, each void extending from a respective opposing end of the pair of perforation lines, such that the voids and the perforation lines define a panel, wherein a respective void is configured for insertion of a digit of a hand of a user, positioning the user for separating the panel from the tube defining an opening;
    a sheet engaged to an inner surface of the tube and extending across the opening; and
    a slit positioned in the sheet, wherein the slit is configured for insertion of digits of the hand of the user, positioning the user for grasping and pulling a respective pad for removing the respective pad from the tube through the slit.

2. The pad storage and dispensing device of claim 1, wherein:
    the tube is cylindrical; and
    the pads are circular.

3. The pad storage and dispensing device of claim 1, wherein the tube comprises paperboard.

4. The pad storage and dispensing device of claim 1, wherein the respective void is arcuate distal from the respective opposing end of the pair of perforation lines.

5. The pad storage and dispensing device of claim 1, wherein the sheet is adhesively engaged to the tube.

6. The pad storage and dispensing device of claim 1, wherein the slit extends from proximate to opposed limits of the opening.

7. The pad storage and dispensing device of claim 1, wherein the sheet comprises elastomer, such that the sheet is resiliently deformable.

8. The pad storage and dispensing device of claim 7, wherein the sheet is substantially transparent.

9. The pad storage and dispensing device of claim 1, further including:
    a tab engaged to and extending from a respective opposed end of the tube; and
    a hole positioned in the tab, the hole being complementary to a rod of a display unit, wherein the hole is configured for selective insertion of the rod for removably engaging the tube to the display unit.

10. The pad storage and dispensing device of claim 9, wherein the tab is perforated proximate to the tube, wherein the tab is configured for being selectively torn from the tube.

11. A method for storing and dispensing pads, the method comprising the steps of:
    providing a pad storage and dispensing device comprising:
        a tube having opposed ends, the opposed ends being closed,
        a plurality of pads positioned in the tube,
        a pair of perforation lines positioned in the tube, the perforation lines of the pair of perforation lines being parallel and perpendicular to the opposed ends,
        a pair of voids positioned in the tube, each void extending from a respective opposing end of the pair of perforation lines, such that the voids and the perforation lines define a panel,
        a sheet engaged to an inner surface of the tube and extending over the voids and the panel, and
        a slit positioned in the sheet;

inserting a digit of a hand of a user into a respective void and in between the panel and the sheet;

separating the panel from the tube;

positioning the tube in a location of use;

inserting digits of the hand of the user through the slit and into the tube; and grasping a respective pad and pulling the respective pad from the tube through the slit.

12. A pad storage and dispensing device comprising:

a tube having opposed ends, the opposed ends being closed, the tube being cylindrical, the tube comprising paperboard;

a plurality of pads positioned in the tube, the pads being circular;

a pair of perforation lines positioned in the tube, the perforation lines of the pair of perforation lines being parallel and perpendicular to the opposed ends, a pair of voids positioned in the tube, each void extending from a respective opposing end of the pair of perforation lines, such that the voids and the perforation lines define a panel, wherein a respective void is configured for insertion of a digit of a hand of a user, positioning the user for separating the panel from the tube defining an opening, the respective void being arcuate distal from the respective opposing end of the pair of perforation lines;

a sheet engaged to an inner surface of the tube and extending across the opening, the sheet comprising elastomer, such that the sheet is resiliently deformable, the sheet being substantially transparent, the sheet being adhesively engaged to the tube;

a slit positioned in the sheet, wherein the slit is configured for insertion of digits of the hand of the user, positioning the user for grasping and pulling a respective pad for removing the respective pad from the tube through the slit, the slit extending from proximate to opposed limits of the opening;

a tab engaged to and extending from a respective opposed end of the tube, the tab being perforated proximate to the tube, wherein the tab is configured for being selectively torn from the tube; and a hole positioned in the tab, the hole being complementary to a rod of a display unit, wherein the hole is configured for selective insertion of the rod for removably engaging the tube to the display unit.

\* \* \* \* \*